(12) United States Patent
Greener et al.

(10) Patent No.: US 6,586,249 B2
(45) Date of Patent: *Jul. 1, 2003

(54) METHOD FOR MORE EFFICIENT ELECTROPORATION

(75) Inventors: Alan L. Greener, San Diego, CA (US); Bruce D. Jerpseth, Cedar Creek, TX (US)

(73) Assignee: Stratagene, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/052,241

(22) Filed: Jan. 15, 2002

(65) Prior Publication Data

US 2002/0164804 A1 Nov. 7, 2002

Related U.S. Application Data

(63) Continuation of application No. 09/531,253, filed on Mar. 17, 2000, now Pat. No. 6,338,965, which is a continuation of application No. 09/253,703, filed on Feb. 22, 1999, now Pat. No. 6,040,184.
(60) Provisional application No. 60/103,612, filed on Oct. 9, 1998.

(51) Int. Cl.$^7$ ................................................. C12N 15/64
(52) U.S. Cl. .................. 435/461; 435/470; 435/471; 435/488; 435/252.3; 435/256.33; 435/440; 435/410; 435/325; 435/254.21
(58) Field of Search ................................ 435/470, 488, 435/461, 252.3, 252.33, 440, 471, 325, 410, 254.21

(56) References Cited

U.S. PATENT DOCUMENTS

| | | | |
|---|---|---|---|
| 5,186,800 A | | 2/1993 | Dower |
| 5,712,135 A | | 1/1998 | D'Halluin et al. |
| 5,879,891 A | | 3/1999 | Thompson |
| 6,040,184 A | * | 3/2000 | Greener et al. ............. 435/461 |
| 6,338,965 B1 | * | 1/2002 | Greener et al. ............. 435/470 |

OTHER PUBLICATIONS

Andreason et al., *Biotechniques*, 6:650–660 (1988).
Andreason et al., *Analytical Biochemistry*, 180:269–275 (1989).
Dower et al., *Nucleic Acids Research*, 16:6127–6145 (1988).
Knutson et al., *Analytical Biochemistry*, 164:44–52 (1987).
Neumann et al., *The EMBO Journal*, 1:841–845 (1982).
Sambrook et al., *Molecular Cloning: A Laboratory Manual*, 1:1.75, 2$^{nd}$ ed., Cold Spring Harbor Laboratory Press (1989).
Sambrook et al., *Molecular Cloning: A Laboratory Manual*, 3:16.54–16.55, 2$^{nd}$ ed., Cold Spring Harbor Laboratory Press (1989).
Taketo, *Biochimica et Biophysica Acta*, 949:318–324 (1988).
Antonov, Peter A. et al., "Heat Shock and Osmotically Dependent steps by DNA uptake after *Escherichia coli* electroporation." *Biochemica et Biophysica Acta*, 1216 (2): 286–288 (1993).
Dunny, Gary M. et al., " Improved Electroporation and Cloning Vector System for Gram–Positive Bacteria." *Applied and Environmental Microbiology*, 57 (4): 1194–1201 (1991).
Schnabel, Jorg, "Protein–Protein Interactions Between Keratin Polypeptides Expressed in the Yeast Two–Hybrid System." *Biochemica et Biophysica Acta*, 1403 (2): 158–168 (1998).
Wei, Ming–Qian, " An Improved Method for the Transformation of Lactobacillus Strains Using Electroporation." *Journal of Microbiological Methods*, 21 (1): 97–109 (1995).
Supplementary European Search Report, for corresponding European Patent Application No. 99 951796.4, mailed Aug. 1, 2002.

* cited by examiner

Primary Examiner—James Ketter
(74) Attorney, Agent, or Firm—Finnegan, Henderson, Farabow, Garrett & Dunner LLP

(57) ABSTRACT

This invention provides improved electroporation methods for transferring nucleic acids of interest into host cells, wherein the host cells are (1) suspended in a substantially non-ionic solution comprising at least one sugar or sugar derivative, (2) mixed with the nucleic acids of interest, and (3) electrically treated. Also, this invention provides for kits used in the method for transferring nucleic acids into host cells.

36 Claims, No Drawings

METHOD FOR MORE EFFICIENT ELECTROPORATION

This application is a continuation application of U.S. patent application Ser. No. 09/531,253, filed Mar. 17, 2000 now U.S. Pat. No. 6,338,965 which is a continuation of U.S. patent application Ser. No. 09/253,703, filed Feb. 22, 1999 now U.S. Pat. No. 6,040,184 which claims the benefit of U.S. Provisional Patent Application No. 60/103,612, filed Oct. 9, 1998. U.S. patent application Ser. No. 09/253,703, filed Feb. 22, 1999, is hereby incorporated by reference in its entirety for any purpose.

The invention relates to the field of electroporation and transformation of host cells, particularly bacterial cells.

BACKGROUND OF THE INVENTION

Introducing nucleic acids into *E. coli* hand other host organisms is central to many types of experiments and analyses. For example, when searching for a gene of interest in a DNA library, the library must be transferred into a host organism. Since the DNA of many organisms is very complex, the number of independent clones that are needed to completely represent the organism is large. In order to create a library that completely represents the organism, the efficiency at which the DNA can be introduced into the host cell becomes limiting. By optimizing this process, the ability to create and screen DNA libraries is facilitated.

Similarly, many other experimental analyses are limited by the ability to introduce DNA into a host organism. When cloning large segments of DNA for whole genome analysis (i.e., using bacterial artificial chromosomes), when performing PCR cloning, or when carrying out random mutagenesis of a gene, followed by cloning all potential altered forms, success often depends on the size of the initial transformation pool. Again, developing conditions that improve the process of introducing nucleic acids into a host organism increases the chance that the experiment will succeed.

There are several methods for introducing nucleic acids into various host cells, e.g., incubating the host cells with co-precipitates of nucleic acids (Graham and van der Eb, *Virology*, 52: 456–467 (1973)), directly injecting genes into the nucleus of the host cells (Diacumakos, *Methods in Cell Biology*, Vol. 7, eds. Prescott, D. M. (Academic Press) pp. 287–311 (1973), introducing nucleic acids via viral vectors (Hamer and Leder, *Cell*, 18: 1299–1302 (1979)), and using liposomes as a means of gene transfer (Fraley et al., *J. Biol. Chem.*, 255: 10431–10435 (1980); Wong et al. *Gene*, 10: 87–94 (1980)). Electroporation has also been used to transform host organisms, including *E. coli*. (Dower et al., *Nucleic Acids Research*, 16: 6127–6145 (1988); Taketo, *Biochimica et Biophysica Acta*, 949: 318–324 (1988); Chassy and Flickinger, *FEMS Microbiology Letters*, 44: 173–177 (1987); and Harlander, *Streptococcal Genetics*, eds. Ferretti and Curtiss (American Society of Microbiology, Washington, D.C.) pp. 229–233 (1987)).

In general, electroporation involves the transfer of genes or gene fragments (nucleic acids) into a host cell by exposure of the cell to a high voltage electric impulse in the presence of the genes or gene fragments (Andreason and Evans, *Biotechniques*, 6: 650–660 (1988)). Quite often, the genes and gene fragments are exogenous, i.e., heterologous to the host organism. Also, frequently the cells have been stored prior to electroporation. A typical method of storage is to freeze the cells. The cells are frozen at a temperature that preserves viability. After thawing those cells, genes or gene fragments may be transferred by electroporation into the cells, permanently or transiently for short-term expression.

An example of a typical electroporation method is to grow bacteria in enriched media (of any sort) and to concentrate the bacteria by washing in a buffer that contains 10% glycerol (Dower et al., 1988, U.S. Pat. No. 5,186,800). As discussed in U.S. Pat. No. 5,186,800, which is hereby incorporated by reference in its entirety, DNA is added to the cells and the cells are subjected to an electrical discharge, which temporarily disrupts the outer cell wall of the bacterial cells to allow DNA to enter the cells.

The electrical treatment to which the host cells are subjected during the process of electroporation is very harsh and typically results in the death of >90% of the host cells. However, it is believed that the majority of cells that survive electroporation take up the nucleic acids of interest. The efficiency with which nucleic acid transfer occurs depends on a variety of factors, including the genetic background of the host cells. Routinely, an efficiency of $10^9$–$1\times10^{10}$ transformants per $\mu g$ of input DNA (plasmid pUC18) may be achieved. Using Rec A- cells, typically $5.0$–$7.0\times10^9$ cells are transformed per $\mu g$ of input DNA. When the host cells are *E. coli*, 10% or less of the treated bacteria survive. However, the percentage is significantly lower for certain strains of *E. coli* that are inefficient at electrotransformation.

In developing and refining electroporation methodology, researchers have identified factors that impact the efficiency of the transfer. These factors include, e.g., the electrical field strength, the pulse decay time, the pulse shape, the temperature in which the electroporation is conducted, the type of cell, the type of suspension buffer, and the concentration and size of the nucleic acid to be transferred (Andreason and Evans, *Analytical Biochemistry*, 180: 269–275 (1988); Sambrook, et al., *Molecular Cloning: a Laboratory Manual*, 2nd Edition, eds. Sambrook, et al. (Cold Spring Harbor Laboratory Press) pp. 1.75 and 16.54–16.55 (1989); Dower et al., (1988); Taketo (1988)). Thus, previous attempts to improve the electroporation efficiency have focused on these factors and thus, have primarily involved manipulation of methods used to prepare the cells, e.g., washing and centrifugation of cells during the processing stage, and methods for applying the electrical shock (i.e., different configuration of the apparatus that delivers the electrical pulse).

Typically, researchers have only modified the host cell suspension materials to aid in freezing the cells before the electrical treatment (Taketo 1988).

SUMMARY OF THE INVENTION

This invention provides improved methods of electroporation and other electrical treatment of cells. The methods comprise the addition of sugars or sugar derivatives, e.g., sugar alcohols, to host cells suspended in a substantially non-ionic solution, either prior to initial freezing, or after thawing, but prior to electrotransformation. The methods of this invention improve electroporation efficiency. The level of improvement is 30% (for cells that generally exhibit higher efficiency) to 300% (for cells that have lower efficiency).

In certain embodiments, at least one sugar or sugar derivative is added to the host cells suspended in a substantially non-ionic solution prior to electrically treating the host cells. Preferably, the sugar or derivative thereof is added in a concentration range of about 0.1% to about 5%. In certain embodiments of the invention, the host cells are suspended in the non-ionic sugar or sugar derivative solution before they are electrically transformed. In certain embodiments, one may prefer to freeze the cells prior to the electrotransformation For instance, one may suspend the host cells in the sugar or sugar derivative solution before freezing the cells. In another instance, the cells may be suspended in the sugar or sugar derivative solution after the cells have been frozen and thawed. In certain embodiments, the host cells are bacterial cells, preferably gram-negative bacterial cells, and most preferably, *E. coli.*

This invention also provides a kit for use in the practice of the above-described methods of transferring nucleic acids of interest into host cells. The electroporation kit includes host cells suspended in a substantially non-ionic solution comprising at least one sugar or sugar derivative. In certain embodiments, the kit includes host cells suspended in a non-ionic solution having a sugar or sugar derivative a concentration of about 0.1% to about 5%. In other embodiments, the kit includes a non-ionic solution comprising a mixture of sugars and sugar derivatives.

DETAILED DESCRIPTION OF THE INVENTION

Thus, this invention provides methods for transferring nucleic acids of interest into host cells, comprising the steps of mixing host cells suspended in a substantially non-ionic solution comprising at least one sugar or sugar derivative with nucleic acids of interest, and subjecting the mixture to electrical treatment, thereby permitting the transfer of the nucleic acids of interest into the host cells.

In certain embodiments of the invention, the non-ionic solution includes glycerol or dimethyl sulfoxide.

As used herein, the term "non-ionic solution" refers to a buffer solution that would have minimal or no ions present. In many instances, non-ionic solutions are also non-polar, therefore, for the purposes of defining terms in this application, solutions that are non-polar are also, non-ionic. The concentration of ions in the buffer is adequately low so that when electricity is discharged into the host cells, little or no additional current is carried into the cells. The presence of ions in the buffer may result in additional current being carried into the cell and can lower the survival rate of the host cells.

A number of sugars and sugar derivatives are known to those skilled in the art. The sugars or sugar derivatives useful in the processes and kits of this invention may be in either the D-stereoisomeric or the L-forms (enantiomers) form. Sugars that may be used in the methods and kits of this invention include, but are not limited to: aldoses, such as monosaccharides which include trioses (i.e. glyceraldehyde), tetroses (i.e. erythrose, threose), pentoses (i.e. arabinose, xylose, ribose, lyxose), hexoses (i.e. glucose, mannose, galactose, idose, gulose, altrose, allose, talose), heptoses (i.e. sedoheptulose), octoses (i.e. glycero-D-manno-octulose), pentose ring sugars (i.e. ribofuranose, ribopyranose); disaccharides (i.e., sucrose, lactose, trehalose, maltose, cellobiose, gentiobiose); and trisaccharides (i.e., raffinose), oligosaccharides (i.e., amylose, amylopectin, glycogen).

Sugar derivatives that may be used in the methods and kits of this invention include, but are not limited to: alditols or aldose alcohol, which include erythritol, glucitol, sorbitol, or mannitol; ketoses, e.g., dihydroxyacetone, erythrulose, ribulose, xylulose, psicose, fructose, sorbose, and tagatose; aminosugars such as glucosamine, galactosamine, N-acetylglucosamine, N-acetylgalactosamine, muramic acid, N-acetyl muramic acid, and N-acetylneuraminic acid (sialic acid); glycosides, such as glucopyranose and methyl-glucopyranose; and lactones, such as gluconolactone.

In certain embodiments of the invention, the non-ionic host cell buffer solution may include a mixture of sugars and derivatives thereof. One skilled in the art would be able to select suitable sugars to place in the mixture and to determine appropriate concentrations of these sugars and sugar derivatives to optimize the invention.

In certain embodiments of the methods and kits of this invention, at least one sugar or derivative thereof is added to host cells suspended in a non-ionic buffer solution prior to electrical treatment of the cells, wherein the concentration of the sugar or derivative thereof is in the range of about 0.1% to about 5%. Preferably, the concentration of the sugar or derivative thereof is about 2.0% to about 2.5%. In specific embodiments, the added sugar derivative is sorbitol and its concentration is about 2.5%.

As used herein, the term "electrical treatment" includes any method of using electrical pulses or electrical discharges to introduce genes, fragments of genes, or other nucleic acids of interest into a cell. Electroporation methods are well known to those skilled in the art (See, e.g., Sambrook et al. 1987; Stratagene Instruction Manual for *Epicurian Coli*® Electroporation-Competent Cells 1997). Conditions for optimal efficiency can be determined by one skilled in the art.

In certain embodiments of the invention, bacterial cells are suspended in the non-ionic buffer solution comprising at least one sugar or sugar derivative prior to electrical treatment. Preferably, the bacterial cells are gram-negative bacterial cells (Davis, B. D et al., *Microbiology: $3^{rd}$ Edition* (eds. Davis, B. D. et al. Harper and Row, 1995)). In a preferred embodiment of the invention, the gram-negative bacterial cells are *E. coli.* In a specific embodiment, the bacterial cell strain is XL1-Blue™ (Stratagene Catalogue #200268).

As used herein, the term "nucleic acids of interest" includes, but is not limited to, nucleic acid sequences that encode functional or non-functional proteins, and fragments of those sequences, polynucleotides, or oligonucleotides. The nucleic acids of interest may be obtained naturally or synthetically, e.g., using PCR or mutagenesis. Further, the nucleic acids may be circular, linear, or supercoiled in their topology. Preferably, the nucleic acids are linear. Although not limited to such sizes, certain embodiments of this invention employ nucleic acids of interest ranging from about 3 kb to about 300 kb, depending on factors well known to those of skill in the art.

As used herein, the term "permitting the transfer of the nucleic acids of interest into the cells" may include transient transfer or permanent incorporation of the nucleic acids of interest into the bacterial cells by either autonomous replication or integration into the genome. One skilled in the art would be able to determine the optimal conditions to transfer the nucleic acids of interest, e.g., length of nucleic acids, pulse, time. Typically, one skilled in the art may subject the host cells to electroporation for a certain period of time, thereby insuring the transfer of nucleic acids, but possibly sacrificing a large number of cells. This invention allows a larger number of host cells suspended in the above-described solutions to survive electroporation than cells suspended in the previously known solutions. Typically, subjecting *E. coli* to electrical transformation caused >90% of the cells to die; however, by practicing the methods of this invention, more of the cells will survive.

One skilled in the art would know how to select an appropriate media to promote growth of the transformed cells. The chosen media should propagate the transformed cells that either transiently express or have nucleic acids integrated into the host cells genome. Further, the media should be selected so as to assist the cells in recovering from the electrical treatment.

This invention also provides kits used in the practice of the methods of transferring nucleic acids into bacterial host cells according to this invention. In certain embodiments, the kits comprise transformation competent host cells suspended in a substantially non-ionic solution comprising at least one sugar or sugar derivative. In certain embodiments the kits, the concentration of the sugar or derivative thereof is in the range of about 0.1% to about 5%. In certain embodiments of the kits of this invention, the transformation competent host cells are bacterial cells, preferably *E. coli*. Other contents of the kit may include a control plasmid DNA for use in determining whether transformation has occurred.

The invention described above may be better understood by reference to the following examples. However, these examples are offered solely for the purpose of illustrating the invention, and should not be interpreted as limiting the invention.

EXAMPLES

Prior to electroporation, *E. coli* cells are usually grown in enriched media and then, suspended in 10% glycerol. The glycerol serves at least two purposes. It is non-polar and thus, does not carry excess electrical charge into the host cells. In addition, the transformation competent host cells typically are stored at temperatures below −70° C. Cell viability during this freezing process is improved if cells are suspended in cryopreservative compounds, e.g., glycerol, dimethyl sulfoxide.

Fermentation and Inoculation

A 15 liter Applikon™ fermenter was thoroughly cleaned with reverse osmosis water. After cleaning, liquid remaining in the fermenter was removed to provide an ion-free environment. Specifically, all traces of magnesium were removed from the fermenter. Media to grow the *E. coli* was produced in the glass vessel of the fermenter by adding 240–280 grams DIFCO™ tryptone, 60–70 grams of DIFCO™ yeast, and 6 grams of NaCl to the empty vessel. 12 L of 0.2 micro filtered water was added to the fermenter. The fermenter was autoclaved on slow exhaust for 35–45 minutes and cooled. After removing the fermenter from the autoclave, it was heated up to 37° C.

XL1-Blue (Stratagene Catalogue #200228) was streaked out on Tet plates and incubated at 37° C. for 24 hours (Sambrook et al. 1987). Since this method may be used to prepare different types of electrocompetent cells, one skilled in the art would know on which plates the different types of cells grow. For example, SURE™ (Stratagene) and XL1-Blue MRF'™ (Stratagene) should be streaked out on Tet plates, TG-1™ on LB plates.

Under sterile conditions, 75–100 ml of magnesium-free SOB (20 grams Tryptone 5 grams yeast extract, and 0.5 grams of NaCl per liter) was poured into three sterile 250 ml flasks. 2–5 bacterial colonies, between 2–5 mm in width, were chosen and inoculated into the magnesium-free SOB. The cells were grown overnight at room temperature in an air shaker at 250–275 rpm.

The optical density (O.D.) of the cells cultured overnight was determined with a Beckman DU640B spectrometer by diluting the cells 1 to 10, i.e., 900 $\mu$l of media was added to a quartz cuvette, the spectrometer was zeroed with the media-filled cuvette, 100 $\mu$l of cells was added to the cuvette, and the O.D. of the cells was determined.

Under sterile conditions, 60–100 O.D. units of the cells were added into the fermenter using an electric pump. The temperature of the fermenter was maintained at 37° C. The temperature to set the fermenter may vary depending on what cells are used. For XL1-Blue™, XL1-Blue MRF'™, and TG-1™ cells, the fermenter should be set at 37° C., and for SURE™ cells, the machine should be set at 38.5–39° C. Those skilled in the art know how to determine the optimal conditions for growing different bacterial cells in a fermenter.

When the O.D. of the fermenter is 0.15–0.25 or when it was no longer possible to see through the fermenter, as much SOB as the fermenter would hold and 1–2 drops of sterile anti-foam A™ (Sigma) were added. To maintain oxygen content, the culture was agitated with airing. The fermentation process took about five hours. One skilled in the art could easily determine the optimal conditions and time frame for harvesting the cells.

At the desired final O.D. 0.82 [Beckman DU640B spec 550 nm], the fermenter was cooled to 4° C. The bacteria was concentrated to 0.5 liters with a mini-sert crossflow filtration unit from Sartorious. When the fluid level inside the fermenter was 0.75 liters, a buffer exchange was set up. The buffer exchange was run until 2.0 gallons of sterile cooled water (4° C.) had been exchanged. Another buffer exchange was run with 1.0 gallon of pre-cooled 0.2 micro filtered water+15% glycerol.

Afterwards, the cells were removed from the fermenter. The cells were split into 2 spin buckets and centrifuged (Sorval Centrifuge™) for 15 minutes at 4,000 rpm at 0° C. The supernate was decanted. 35 ml of 15% glycerol/water was poured into the spin buckets and the pellets were pipetted into solution as quickly as possible. After solubilizing the pellet, the solutions were combined into one spin bucket. The cells were aliquoted in 100 $\mu$l batches and placed in a −80° C. freezer for storage.

Additives Added to the Competent Bacterial Cell Preparation

The effect of non-polar aldoses and aldose alcohols was tested to see if those compounds improved the electroporation efficiency in *E. coli*. Specifically, galactose (an aldohexose monosaccharide), maltose (an aldohexose disaccharide), mannitol (an aldohexose alcohol), and sorbitol (an aldohexose alcohol) additives were tested.

After two hours of freezing, competent cells were thawed and amounts varying between 0.1% and 5.0% of various sugar or sugar aldoses were added to the thawed cells. 1 $\mu$l of 10 pg/$\mu$l plasmid, pCMV-Script (Stratagene #211199) in TE buffer or water (or other low-ionic strength buffer) was added to 40 $\mu$l of the treated cells in a chilled 1.5 ml Microfuge tube. The cells were gently mixed and chilled.

The DNA-cell mixture was transferred to a chilled electroporation cuvette. The cuvette was pulsed once, using a Bio-Rad II Gene Pulsar, at 1.7 kV (kilo Volts), 200$\Omega$ and 25 $\mu$F. The cuvette was immediately removed and 960 $\mu$l of SOC medium (2 ml of 20% glucose and 1 ml of 2M Mg per 100 ml of SOB medium) was added to resuspend the cells.

That suspension was transferred to a sterile 15-ml Falcon 2059 polypropylene tube and shaken at 225–250 rpm at 37° C. for 1 hour. We pipetted 2.5 $\mu$l of transformed cells into a 100 $\mu$l pool of SOC medium on an Amp plate (Sambrook et al. 1997). The cell/media mixture was spread over the Amp plates. The plates were incubated overnight (16–20 hours) at 37° C.

The treated cells demonstrated an improvement in transfer efficiency. See Table 1.

Sorbitol Concentrations Added to Competent Bacterial Cell Preparation

The effect of adding sugars, prior to freezing the cells, was tested for improved electroporation efficiency. Sorbitol was chosen as the first test compound.

To determine the optimal concentration of sorbitol, the above protocol was followed to produce electrocompetent bacterial cells. However, before freezing the cells, a solution of sorbitol was added such that the final concentrations of the suspension of cells varied from 0%, 1.0%, 2.0%, and 2.5%.

1 μl of 10 pg/μl plasmid, pUC18 (New England Biolabs) in TE buffer or water (or other low-ionic strength buffer), was added to 40 μl of the treated cells in a chilled 1.5 ml Microfuge tube. Transformed cells were obtained by following the above protocol. Various experiments were run to determine the efficiency of transformation. Five different preparations were tested in triplicate, and each preparation was plated in duplicate. See Table 2.

TABLE 1

The Effect of Different Additives on Bacterial Cells in Electroporation Experiments

| Additive | final concentration | Relative efficiency* |
|---|---|---|
| None | — | 1.00 |
| galactose | 0.5% | 2.20 |
|  | 1.0% | 1.50 |
|  | 2.0% | 2.40 |
| maltose | 1.0% | 1.50 |
|  | 2.5% | 3.00 |
|  | 3.0% | 1.30 |
|  | 4.0% | 1.50 |
| mannitol | 0.75% | 3.00 |
|  | 1.00% | 2.80 |
|  | 1.25% | 3.30 |
|  | 2.00% | 2.90 |
|  | 2.20% | 2.80 |
|  | 2.40% | 1.90 |
| sorbitol | 0.75% | 2.20 |
|  | 1.00% | 2.80 |
|  | 1.50% | 3.10 |
|  | 2.00% | 1.50 |

*Relative efficiency was determined by the number of colonies obtained in cells with sugar additives divided by colonies in cells without additive.

TABLE 2

EFFECT OF SORBITOL ADDITIVE ON XL1 - BLUE CELLS IN ELECTROTRANSFORMATION

| Percent sorbitol | Efficiency (cfu/ug pUC18) |
|---|---|
| Experiment #1 | |
| 0% | $9.0 \times 10^9$ |
| 1.0% | $9.3 \times 10^9$ |
| 2.0% | $1.2 \times 10^{10}$ |
| 2.5% | $1.6 \times 10^{10}$ |
| Experiment #2 | |
| 0% | $8.72 \times 10^9$ |
| 1.0% | $1.23 \times 10^{10}$ |
| 2.0% | $1.66 \times 10^{10}$ |
| 2.5% | $1.48 \times 10^{10}$ |
| Experiment #3 | |
| 0% | $9.26 \times 10^9$ |
| 1.0% | $1.03 \times 10^{10}$ |
| 2.0% | $1.23 \times 10^{10}$ |
| 2.5% | $1.33 \times 10^{10}$ |
| Experiment #4 | |
| 0% | $7.10 \times 10^9$ |
| 1.0% | $9.00 \times 10^9$ |
| 2.0% | $1.29 \times 10^{10}$ |
| 2.5% | $1.39 \times 10^{10}$ |

TABLE 2-continued

EFFECT OF SORBITOL ADDITIVE ON XL1 - BLUE CELLS IN ELECTROTRANSFORMATION

| Percent sorbitol | Efficiency (cfu/ug pUC18) |
|---|---|
| Experiment #5 | |
| 0% | $8.89 \times 10^9$ |
| 1.0% | $9.27 \times 10^9$ |
| 2.0% | $1.60 \times 10^{10}$ |
| 2.5% | $1.60 \times 10^{10}$ |

*In each experiment, electroporations were performed in triplicate and each sample was plated in duplicate. Numbers represent the average of 6 values and the standard deviations were less than 10%.

All documents referenced in this application, including but not limited to, articles, books, reviews, patents, and patent applications, are hereby incorporated by reference in their entirety into this specification.

ADDITIONAL REFERENCES

1. Greener, A., *Strategies,* 6:7–9 (1993).
2. Greener, A., *Strategies,* 3:5–6 (1990).
3. Bullock, W. O., Fernandex, J. M., and Short, J. M., *Biotechniques,* 5:81–83 (1987).
4. Jerpseth, B., Greener, A., Short, J. M., Viola, J., and Kretz, P. L., *Strategies,* 5:81–83 (1992).

What is claimed is:

1. A method for transferring nucleic acids of interest into: competent host cells, comprising the steps of:
   (a) mixing competent host cells suspended in a substantially non-ionic solution comprising at least one sugar or sugar derivative with the nucleic acids of interest; and
   (b) subjecting the host cells to an electrical treatment, thereby permitting the transfer of the nucleic acids of interest into the bacterial cells.

2. The method of claim 1, wherein the non-ionic solution further comprises glycerol or dimethyl sulfoxide.

3. The method of 1, further comprising the step of culturing the transformed cells in a selected media capable of promoting their growth.

4. The method according to claim 1, wherein the concentration of the sugar or derivative is in the range of about 0.1% to about 5%.

5. The method according to claim 1, wherein the sugar or sugar derivative is sorbitol in a concentration range of about 2.0 to about 2.5%.

6. The method according to claim 1, wherein the sugar or sugar derivative is an aldose.

7. The method according to claim 6, wherein the aldose is selected from the group consisting of monosaccharides, disaccharides, trisaccharides, and oligosaccharides.

8. The method according to claim 1, wherein the sugar or sugar derivative is an aldose alcohol.

9. The method according to claim 8, wherein the aldose alcohol is selected from the group consisting of erythritol, sorbitol, and mannitol.

10. The method according to claim 1, wherein the sugar or sugar derivative is a ketose.

11. The method according to claim 10, wherein the ketose is selected from the group consisting of dihydroxyacetone, erythrulose, ribulose, xylulose, psicose, fructose, sorbose, and tagatose.

12. The method according to claim 1, wherein the sugar or sugar derivative is an aminosugar.

13. The method according to claim 12, wherein the aminosugar is selected from the group consisting at least one of glucosamine, galactosamine, N-acetylglucosamine, N-acetylgalactosamine, muramic acid, N-acetyl muramic acid, and sialic acid.

14. The method according to claim 1, wherein the sugar or sugar derivative is a glycoside.

15. The method according to claim 14, wherein the glycoside is selected from the group consisting of glucopyranose and methyl-glucopyranose.

16. The method according to claim 1, wherein the sugar or derivative thereof is a lactone.

17. The method according to claim 16, wherein the lactone is gluconolactone.

18. The method according to claim 1, wherein the non-ionic solution comprises a mixture of sugars and sugar derivatives.

19. An electroporation kit comprising transformation competent cells suspended in a substantially non-ionic solution comprising at least one sugar or sugar derivative.

20. The kit according to claim 19, wherein the sugar or derivative thereof is a lactone.

21. The kit according to claim 20, wherein the lactone is gluconolactone.

22. The kit according to claim 19, wherein the transformation competent cells are gram-negative bacterial cells.

23. The kit according to claim 19, wherein the bacterial cells are *E. coli*.

24. The kit according to claim 19, wherein the concentration of the sugar or derivative thereof is in the range of about 0.1% to about 5%.

25. The kit according to claim 19, wherein the sugar or sugar derivative is sorbitol in a concentration range of about 2.0 to about 2.5%.

26. The kit according to claim 19, wherein the sugar or sugar derivative is an aldose.

27. The kit according to claim 26, wherein the aldose is selected from the group consisting of monosaccharides, disaccharides, trisaccharides, and oligosaccharides.

28. The kit according to claim 19, wherein the sugar or sugar derivative is an aldose alcohol.

29. The kit according to claim 28, wherein the aldose alcohol is selected from the group consisting of erythritol, sorbitol, and mannitol.

30. The kit according to claim 19, wherein the sugar or sugar derivative is a ketose.

31. The kit according to claim 30, wherein the ketose is selected from the group consisting of dihydroxyacetone, erythrulose, ribulose, xylulose, psicose, fructose, sorbose, and tagatose.

32. The kit according to claim 19, wherein the sugar or sugar derivative is an aminosugar.

33. The kit according to claim 32, wherein the aminosugar is selected from the group consisting at least one of glucosamine, galactosamine, N-acetylglucosamine, N-acetylgalactosamine, muramic acid, N-acetyl muramic acid, and sialic acid.

34. The kit according to claim 19, wherein the sugar or sugar derivative is a glycoside.

35. The kit according to claim 34, wherein the glycoside is selected from the group consisting of glucopyranose and methyl-glucopyranose.

36. The kit according to claim 19, wherein the non-ionic solution comprises a mixture of sugars and sugar derivatives.

* * * * *